United States Patent [19]

Smirnov et al.

[11] 4,202,314
[45] May 13, 1980

[54] DEVICE FOR INJECTION OF MEDICINAL PREPARATIONS

[76] Inventors: Boris A. Smirnov, ulitsa Borisa Galushkina, 17, kv.26, Moscow; Valery P. Busygin, Zheleznodorozhny proezd, 13, kv. 25, Moskovskaya Oblast, Krasnogorsk; Lidia S. Komina, Yaroslavskoe shosse, 127, kv. 30, Moscow; Vyacheslav N. Mochalov, Prospekt Mira, 122, kv. 174, Moscow; Lev V. Shagalov, Malaya Schukinskaya ulitsa, 15, kv. 89, Moscow; Evgeny A. Gruzdev, ulitsa Gabricheskogo, 4, kv. 49, Moscow, all of U.S.S.R.

[21] Appl. No.: 962,204

[22] Filed: Nov. 20, 1978

[51] Int. Cl.² .............................................. A61M 5/00
[52] U.S. Cl. .............................................. 128/218 F
[58] Field of Search .......... 128/218 R, 218 F, 218 M, 128/221, 220, 213, 215, 216, 272.1

[56] References Cited

U.S. PATENT DOCUMENTS

| 2,752,918 | 7/1956 | Uytenbogaart | 128/218F |
| 2,866,458 | 12/1958 | Hein, Jr. | 128/218 F |
| 3,066,670 | 12/1962 | Stauffer | 128/218 F |
| 3,403,679 | 10/1968 | Sinclair et al. | 128/218 F |

FOREIGN PATENT DOCUMENTS

| 1079275 | 9/1958 | Fed. Rep. of Germany | 128/218 F |
| 1491699 | 10/1969 | Fed. Rep. of Germany | 128/218 F |

Primary Examiner—John D. Yosko
Attorney, Agent, or Firm—Lackenbach, Lilling & Siegel

[57] ABSTRACT

The device for injection of medicinal preparations, according to the invention, comprises a changeable isolated capsule, an injection needle, and a drive to move pistons, made in the form of a spring-loaded pusher located inside the housing which supports the changeable isolated capsule. The housing has a stopping member to arrest said spring-loaded pusher. Inside said isolated capsule, installed coaxially therewith and with each other are a main piston closed by a partition on the side facing the chamber holding the first medicinal preparation and an additional piston. The partition is movable. The injection needle is installed inside the isolated capsule, fixed on the additional piston, and it in use passes through said partition, and has an aperture in the zone of the partition on the side of the chamber holding the first medicinal preparation. The additional piston is located in the channel of the main piston and limits the chamber for the second medicinal preparation. The drive of the pistons has an additional spring-loaded pusher interacting with the additional piston and is located coaxially with the spring-loaded pusher. The housing of the drive of the pistons has an additional stopping member for the additional spring-loaded pusher.

1 Claim, 1 Drawing Figure

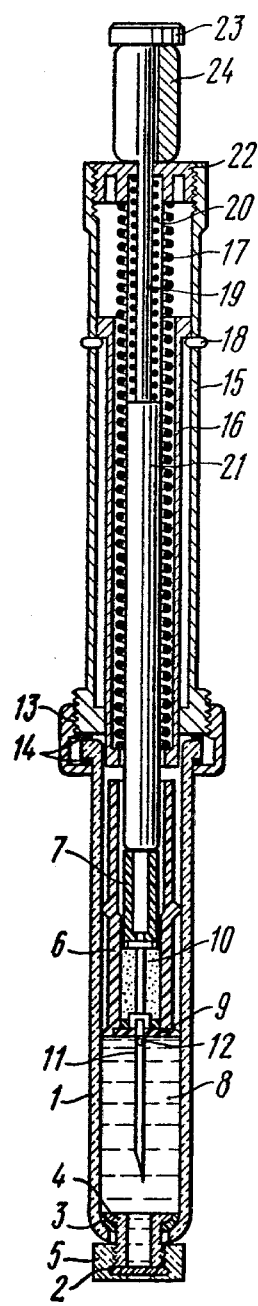

DEVICE FOR INJECTION OF MEDICINAL PREPARATIONS

FIELD OF THE INVENTION

This invention relates to medical equipment and more particularly it relates to a device for administration of medicinal preparations.

This invention can advantageously be used for mixing, immediately before injection, of two or more medicinal preparations, one of which is in the liquid state and the other, or others, are in the powdered or liquid form, and for subsequent subcutaneous injection of the obtained suspension or solution.

The device makes it possible to store separately, in sterile conditions, medicinal preparations, which are mixed immediately before the injection, and to introduce the freshly prepared solution into the body tissue.

BACKGROUND OF THE INVENTION

Known in the prior art is a device for administration of medicinal preparations (cf. U.S. Pat. No. 4,055,177, Nov. 25, 1977), comprising a tube, or capsule, confined, on the bottom, by a membrane and separated by a partition and a needle holder into two chambers A and B, a needle unit, and a piston onto which a rod is screwed.

As the rod is pressed upon, the partition moves under the action of the liquid pressure in the chamber A, the partition is punctured against the needle point and broken. The liquid passes through a hollow needle into the chamber B containing the liquid or solid component. As soon as the whole amount of the liquid is passed into the chamber B the cap is removed to release the injection needle the inner end of which breaks the membrane under the action of a spring.

The known injector for administration of medicinal preparations is inconvenient for auto-injection. The sterility of the injection needle cannot be guaranteed. Moreover, the procedure by which the injector is prepared for use is complicated since it is necessary to mix the components by hand, and residual quantities of the liquid can remain in the chamber A. An additional operation dealing with removal of the cap from the needle is also required before the injection. Furthermore, the capsule of the device contains a certain amount of air between the chambers A and B, which is undesirable and should not be injected with the medicinal preparation.

An object of the invention is to provide a device for administration of medicinal preparations, in which the medicinal ingredients can be mixed semiautomatically before injection.

Another object of the invention is to provide a device for administration of medicinal preparations, which will allow convenient auto-injection with the needle remaining sterile.

The invention resides in a device for administration of medicinal preparations, comprising an isolated capsule, inside which, coaxially arranged therewith and with each other are: a main piston limiting a chamber for the first medicinal preparation, and having a channel to pass the second medicinal preparation. The channel is closed by a partition on the side facing the chamber for the first medicinal preparation. An additional piston, and an injection needle, and a drive of the piston made in the form of a spring-loaded pusher are located inside the housing upon which is installed the changeable isolated capsule and inside which there is a stopping member to arrest the spring-loaded pusher. In accordance with the invention, the partition is installed movably, the injection needle is located inside the isolated capsule, and is fixed to the additional piston, passes through the partition and has an aperture in the zone of the partition on the side of the chamber for the first medicinal preparation. The additional piston is located in the channel of the main piston and confines the chamber for the second medicinal preparation, the drive of the pistons has an additional pusher interacting with the additional piston and located coaxially with the spring-loaded pusher, and the pistons drive housing has an additional stopping member to check the movement of the additional spring-loaded pusher.

The design of the device for administration of medicinal preparation ensures separate storage in sterile conditions of medicinal preparations before mixing them, mixing the medicinal preparations semiautomatically by releasing the stopping member of the spring-loaded pusher before the injection, and also provides semiautomatic conditions for auto-injection by releasing the additional stopping member of the additional spring-loaded pusher.

Moreover, the needle remains sterile during all manipulations.

BRIEF DESCRIPTION OF THE ACCOMPANYING DRAWING

For a better understanding of the invention it will be described in greater detail with reference to its practical embodiment, taken in conjunction with the sole FIGURE of the drawing which shows schematically in cross-section a device for administration of medicinal preparations.

DETAILED DESCRIPTION OF THE INVENTION

The proposed device for administration of medicinal preparations comprises an isolated capsule 1 made of a transparent material and sealed hermetically by elastic gaskets 2 and 3. The gasket 3 is arranged between a threaded sleeve 4 and the isolated capsule 1, while the gasket 2 is located in a nut 5 which is connected with the sleeve 4.

Located inside the isolated capsule 1 coaxially therewith and with each other are a main piston 6 and an additional piston 7. The main piston 6 confines a chamber 8 holding the first medicinal preparation (liquid) and has a channel to pass the second medicinal preparation, closed by a partition 9 on the side facing the chamber 8 for the first medicinal preparation. The partition 9 is movably installed. The additional piston 7 is located in the channel of the main piston 6 and confines a chamber 10 holding the second medicinal preparation (dry substance). An injection needle 11 is located inside the isolated capsule 1, and it is fixed on the additional piston 7, passes through the partition 9 and has an aperture 12 in the zone of the partition 9, on the side of the chamber 8 for the first medicinal preparation.

The isolated capsule 1, by means of a nut 13 and two gaskets 14, is secured on a housing 15 installed wherein is the drive of the pistons 6 and 7, made in the form of a pusher 16 with a spring 17. The housing 15 has a stopping member, in the form of an arrester 18, for the pusher 16. The drive of the pistons 6 and 7 has an additional pusher 9 interacting with the additional piston 7 and located coaxially with the spring-loaded pusher 16.

The additional pusher 19 with a spring 20 installed in a tube 21 is rigidly connected with the nut 22, and is arranged inside the spring-loaded pusher 16. The end the additional pusher 19 bears a nut 23. The housing 15 of the drive of the pistons 6 and 7 has an additional stopping member made in the form of an arrester 24 for the additional spring-loaded pusher 19. The arrester 24 is located between the nuts 22 and 23 on an additional pusher 19, while the arrester 18, that fixes the spring-loaded pusher 16, enters the slots of the housing 15 of the drive of the pistons 6 and 7.

The device for administration of medicinal preparations as shown in the drawing is ready for operation and operates as follows.

The nut 5 is pressed against the muscle tissue into which the medicinal preparation is to be injected, and the arrester 24 is released. Subsequently, the additional pusher 19, acted upon by the spring 20, moves the additional piston 7. The movable partition 9, together with the injection needle 11, moves into the chamber 8 containing the first medicinal preparation to open the chamber 10 containing the second medicinal preparation which then enters the chamber 8 to mix with the first medicinal preparation. The injection needle 11 then punctures the elastic gasket or partition 2 and penetrates the muscle tissue.

The arrester 18 is now released to actuate the pusher 16 which is acted upon by the spring 17. The pusher presses the main piston 6 of the isolated chamber 1 to press out the medicinal mixture from the chamber 8 of the isolated capsule 1, through the aperture 12 of the needle 11, of a patient or individual into the flesh.

As soon as the whole dose of the medicinal preparation has been injected, the injection needle 11 is withdrawn, together with the isolated capsule 1. The nut 13 is undone, the additional pusher 19 and the pusher 16 of the drive of the pistons 6 and 7 are set in the initial position, and fixed by the arresters 18 and 24. A new isolated or separate changeable capsule 1 is attached now to the housing 15 holding the drive of the pistons 6 and 7 and such new capsule 1 is then ready for use as before.

Although the present invention has been described in some detail by way of illustration and example for purposes of clarity of understanding, it will, or course, be understood that various changes and modifications may be made in the form, details, and arrangements of the parts without departing from the scope of the invention as set forth in the following claims.

What is claimed is:

1. A device for administration of medicinal preparations comprising:
   a changeable isolated capsule;
   a main piston installed coaxially inside said isolated capsule, and confining a chamber for a first medicinal preparation and having a channel to pass a second medicinal preparation;
   a movably installed partition closing the channel for the second medicinal preparation on the side facing the chamber holding the first medicinal preparation;
   an additional piston installed in the channel of said main piston, confining the chamber for the second medicinal preparation;
   an injection needle installed inside said changeable isolated capsule fixed on said additional piston, passing through said partition and having an aperture in the zone of said partition;
   a housing upon which the changeable isolated capsule is installed;
   a drive of the pistons, installed in said housing;
   a spring-loaded pusher of said drive of the pistons, interacting with said main piston;
   an additional spring-loaded pusher of said drive of the pistons, interacting with said additional piston and arranged coaxially with said spring-loaded pusher;
   a stopping member, in said housing for the spring-loaded pusher; and
   an additional stopping member installed in the housing for said additional spring-loaded pusher.

* * * * *